United States Patent
Oriel et al.

[11] Patent Number: 5,834,297
[45] Date of Patent: Nov. 10, 1998

[54] METHOD FOR PRODUCTION OF INDIGO AND INDIRUBIN DYES

[75] Inventors: Patrick J. Oriel, Midland, Mich.; In Cheol Kim, Taejeon, Rep. of Korea

[73] Assignee: Board of Trustees operating Michigan State University, East Lansing, Mich.

[21] Appl. No.: 876,365

[22] Filed: Jun. 16, 1997

Related U.S. Application Data

[62] Division of Ser. No. 546,829, Oct. 23, 1995, Pat. No. 5,691,171.

[51] Int. Cl.⁶ ............ C12N 15/03; C12N 1/21; C12N 15/63; C07H 21/04
[52] U.S. Cl. ............ 435/252.31; 435/252.8; 435/320.1; 536/23.2
[58] Field of Search ............ 435/320.1, 252.31; 536/23.1

[56] References Cited

U.S. PATENT DOCUMENTS

| 4,520,103 | 5/1985 | Ensley | 435/121 |
| 4,894,337 | 1/1990 | Oriel et al. | 435/156 |
| 5,112,747 | 5/1992 | Van Grinsven et al. | 435/121 |

OTHER PUBLICATIONS

Dong F et al., Applied and Environmental Microbiology, vol. 58, No. 8, pp. 2531–2535, 1992.

Gurujeyalakshmi, G. et al., Appl. Environ. Microlbiol. 55:500–502 (1989).

Hart et al, Microbiology 138 211–216 (1992).

Kim and Oriel, Applied and Environmental Microbiology 61 1252–1256 (1995).

Dower, W. J., et al., Nucleic Acids Res. 16:6127–6139 (1988).

Primary Examiner—Eric Grimes
Assistant Examiner—Peter P. Tung
Attorney, Agent, or Firm—Ian C. McLeod

[57] ABSTRACT

A method for the production of indigo and indirubin dyes using a recombinant *Escherichia coli* containing a gene encoding a phenol hydroxylase from *Bacillus stearothermophilus*. The dyes are used for coloring cloth and the like.

12 Claims, 7 Drawing Sheets

FIG. 6A

```
Q   I   V   E   N   W   D   T   M   G   L   R   A   S   G   S   N   G   V   L          200
GTGAAGGTGCTTATGTTCCATTACACGGATCTTCCGGCTGGCTCTAATGGTGATGGCTCAT                           660
 V   E   G   A   Y   V   P   L   H   R   I   F   P   A   G   R   V   M   A   H          220
GGGAAGCCAGTGGAGGCGATTACGACGAGGCGATTACGAGAATGATCCGTATATCGCATGCCATTTATG                   720
 G   K   P   V   G   G   D   Y   D   E   N   D   P   V   Y   R   M   P   F   M          240
CCGCTTTCTTGCTTGGGTTCCCTTTAGTATCTTTAGGCGGCGACGATTGTTAGGCGACGATTGTGTCA                    780
 P   L   F   L   L   G   F   P   L   V   S   L   G   G   D   E   R   L   V   S          260
CTTTTCCAAGAACGCACTGAGAAGGCATTCGTGTCTTCAAGGGCGCGAAAGAAAG                                 840
 L   F   Q   E   R   T   E   K   R   I   R   V   F   K   G   G   A   K   E   K          280
GATTCTGCCGCTAGCCAGGGCTGTTAGCCGAGATGAAAACAGAATTAAATGCAATGGAA                             900
 D   S   A   A   S   Q   R   L   L   A   E   M   K   T   E   L   N   A   M   E          300
GGCATTGTGAACAATATCCGCGAGAGCAGCTTGAGGCTTGCCAAAAAGAAGGAAAGACGGTG                          960
 G   I   V   E   Q   Y   I   R   Q   L   E   A   C   Q   K   E   G   K   T   V          320
ATGAACGATATGGAGCGAGAACACTGTTAACTCTGTGGAGGCAATTCGATCTTTAAAGGCGAT                         1020
 M   N   D   M   E   R   E   Q   L   F   A   W   R   G   Y   V   A   K   A   S          340
GCCAATATTGCCGTCAGAACACTGTTAACTCTGTTGGAGGCAATTCGATCTTTAAAGGCGAT                          1080
 A   N   I   A   V   R   T   L   L   T   L   G   G   N   S   I   F   K   G   D          360
CCGGTAGAACTGTTCACAAGAGATTTGCTAGCGGTGGCCCGCACATCCTAACTCCCTGTGG                           1140
 P   V   E   L   F   T   R   D   L   L   A   V   A   A   H   P   N   S   L   W          380
GAGGATGCGATGGCTGCATATGGAAGAACGATATTCGGGCTGCCAGGGACCCAGTCTGG                             1200
 E   D   A   M   A   A   Y   G   R   T   I   F   G   L   P   G   D   P   V   W          400
TAAGACAGCAGCAGAATGTGTGTTATAAGATTTTCAAAAAATTCATTTCTTTGGTGAA                              1260
 * * *
AGAAAATGGATTTCACACAAATTAAACACAGAAAAGGAGACGGATACCGTGGATGACCGTTGT                          1320
TTCACCAATATACAAAAAACAGAAAAATTAAACACAGAAAAGGAGACGGATACCGTGGATGACCGTTGT                    1380
TTCGCAACGTAATGGGGACATTTGCCACAGGGGTGACAGTCATAACGACAGAGATCGACG                             1440
GGGATATACACGGCATGACTGCAAATGCGTTTATGTCCGTATCGTTACATCCAAAATTGG                             1500
TGCTTATTTCGATTGGCGAAAAGCAAAGATGCGGGAGCGTATCAAAAATCGAAAACGT                               1560
ATGCAGTAAGCTT                                                                            1573
```

FIG. 6B

METHOD FOR PRODUCTION OF INDIGO AND INDIRUBIN DYES

This is a divisional of application Ser. No.08/546,829 filed on Oct. 23, 1995, now U.S. Pat. No. 5,691,171.

BACKGROUND OF THE INVENTION

(1) Field of the Invention

The present invention relates to a method for the production of indigo and indirubin dyes using a novel recombinant *Escherichia coli* containing a gene encoding a phenol hydroxylase from *Bacillus stearothermophilus*. The dyes are used for coloring cloth and the like as is well known to those skilled in the art.

(2) Description of Related Art

Aerobic thermophilic bacteria are a subject of research attention as a result of interest in their evolution, survival mechanisms, and potential for biotechnological utilization. *Bacillus stearothermophilus* is a well known bacterium of this type. Degradation of phenol by a *Bacillus stearothermophilus* has been described in the prior art (Gurujeyalakshmi, G., et al., Appl. Environ. Microbiol. 55:500–502 (1989)).

U.S. Pat. No. 4,894,337 to Oriel et al., one of the inventors herein, describes *Bacillus stearothermophilus* BR219 which is deposited under the Budapest Treaty as ATCC 67824. This strain produces a phenol hydroxylase which converts a benzene ring compound (phenol) to a cyclic hydroxide (pyrocatechol).

U.S. Pat. No. 4,520,103 to Ensley describes a method for production of indigo with a recombinant bacterium in a medium which is indole free. Use of specific strains of a recombinant *E. coli* to produce indigo or indigotin from indole is particularly described using a gene encoding an aromatic dioxygenase from another bacterium to convert the indole. Indirubin production is not described. Indole preparation is described in U.S. Pat. No. 5,112,747 to Van Grinsven et al. Hart et al (Microbiology 138 211–216 (1992) described a recombinant *E. coli* containing a cloned Rhodococcus gene for producing indigo and indirubin. Indole is produced which is oxidized to indigo.

The formula for indole is:

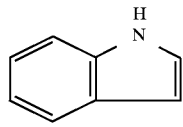

The formula for indigo is:

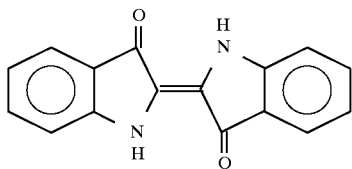

As can be seen the conversion to indigo requires a condensation of two moles of indole. The same type of condensation is required for forming indirubin which is an isomer having the formula:

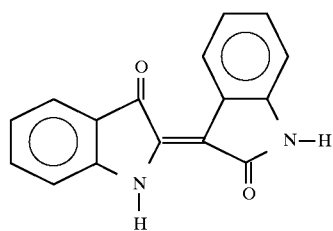

It is likely that all conversions first require the formation of indole or a closely related compound.

OBJECTS

It is therefore an object of the present invention to provide a novel method for the preparation of indigo and indirubin. Further, it is an object of the present invention to provide novel bacteria, plasmids and DNA involved in the conversion. Further still, it is an object of the present invention to provide a method for producing indigo and indirubin which is relatively easy to perform and inexpensive. These and other objects will become increasingly apparent by reference to the following description and the drawings.

BRIEF DESCRIPTION OF THE DRAWINGS

FIG. 6A and 6B show the nucleotide and deduced amino acid sequence of the phenol hydroxylase gene (SEQ ID NO. 1; pheA). The nucleotide sequence was numbered from the first nucleotide for translation initiation. A putative promoter (−35 and −10 region) and probable Shine-Dalgarno sequence are indicated by boldface type. The inverted repeat sequence upstream and downstream of the coding region are marked with a dashed line.

DESCRIPTION OF PREFERRED EMBODIMENTS

A process for preparation of indigo and indirubin dyes which comprises: growing a recombinant *Escherichia coli* containing a gene from *Bacillus stearothermophilus* encoding phenol hydroxylase in an aqueous growth medium so that indigo and indirubin are produced from the indole.

The cells are grown in an aqueous growth medium preferably containing the phenolic compound, preferably phenol, cresols or chlorophenol as an inducer for phenol hydroxylase. Preferably the phenolic compound is present in an amount between about 0.001 and 10 mM. The yield of the phenol hydroxylase is increased in this manner. Also included is a carbon source, a nitrogen source and minerals. A preferred growth medium is LB which contains yeast extract, sodium chloride and tryptone.

Various organic solvents can be used to extract the indigo and indirubin dyes expressed by or in the cells of the recombinant *E. coli*, such as chloroform and ethyl acetate and other solvents for the indigo and indirubin. The cells can optionally be disrupted by various techniques such as sonication or freezing. The indirubin and indigo can be separated chromatographically by various well known methods.

The present invention also relates to an isolated and purified DNA encoding a phenol hydroxylase having a DNA sequence essentially as set forth in SEQ ID NO:1.

The present invention also relates to a recombinant plasmid containing a segment of DNA encoding a phenol hydroxylase having a sequence essentially as set forth in SEQ ID NO: 1.

The present invention also relates to an *Escherichia coli* containing a recombinant plasmid containing a segment of DNA having a sequence essentially as set forth in SEQ ID NO:1.

The present invention also relates to a recombinant plasmid containing a segment of DNA encoding an isolated and purified phenol hydroxylase wherein the DNA is contained in plasmid pGG01 of *Bacillus stearothermophilus* deposited as ATCC 67824.

The present invention also relates to an *Escherichia coli* containing a recombinant plasmid containing a segment of DNA encoding an isolated and purified phenol hydroxylase, wherein the DNA used to produce the recombinant is contained in plasmid pGG01 of *Bacillus stearothermophilus* deposited as ATCC 67824.

Figure 1:
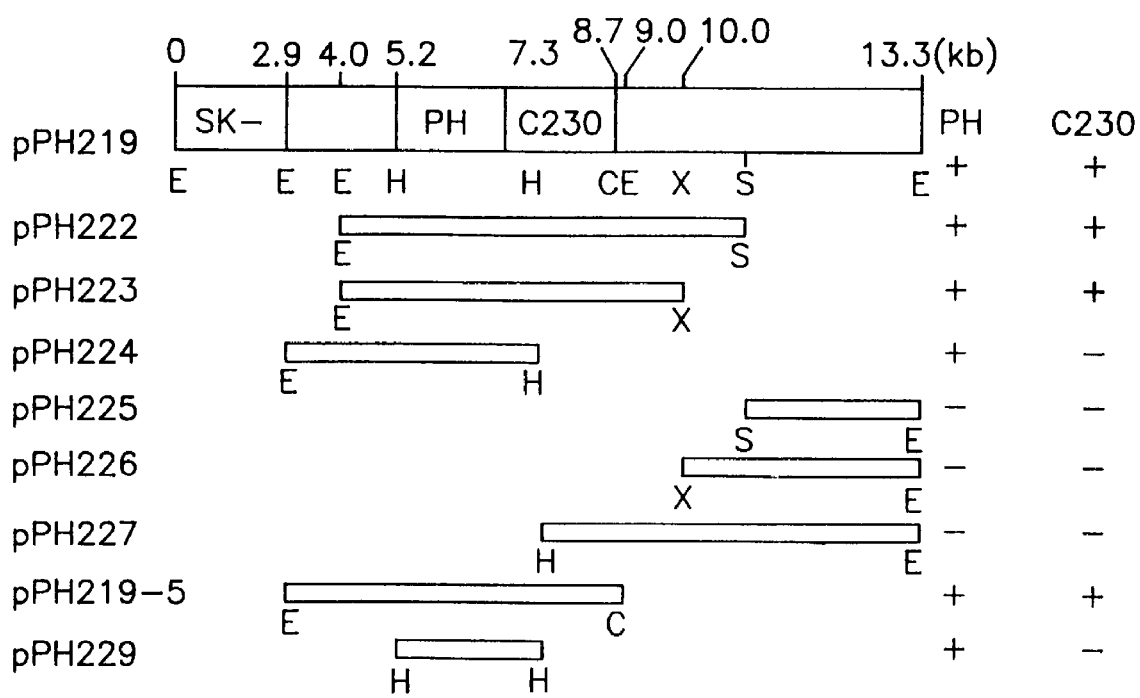
FIG. 1 is a restriction enzyme map of plasmid pPH219 and its derivatives. The ability (+) or inability (−) of the plasmids to produce phenol hydroxylase (PH) and/or catechol 2,3-dioxygenase (C230) is indicated to the right of the restriction enzyme maps. Abbreviations: E, EcoRI; C, ClaI; H, HindIII; X, XhoI; S, SalI. Approximate positions of the phenol hydroxylase and catechol 2,3-dioxygenase genes deduced from this data are shown in the top line of boxes.

The present invention also relates to *Escherichia coli* containing plasmid pPH229 was deposited under the Budapest Treaty as ATCC 69891 at the American Type Culture Collection, Rockville, Md. It is available upon request by name and deposit number. Plasmid pPH229 which encodes for phenol hydroxylase pH as shown in FIG. 1. *Bacillus stearothermophilus* ATCC 67824 is also deposited under the Budapest Treaty. This strain is described in U.S. Pat. No. 4,894,337 to Oriel et al. A publication by the inventors herein described the phenol hydroxylase gene (Kim and Oriel, Applied and Environmental Microbiology 61 1252–1256 (1995)).

The phenol hydroxylase (PH) is isolated from cells of the *Bacillus stearothermophilus*. It can be purified by conventional techniques such as affinity chromatography and gel electrophoresis.

Figure 6A:
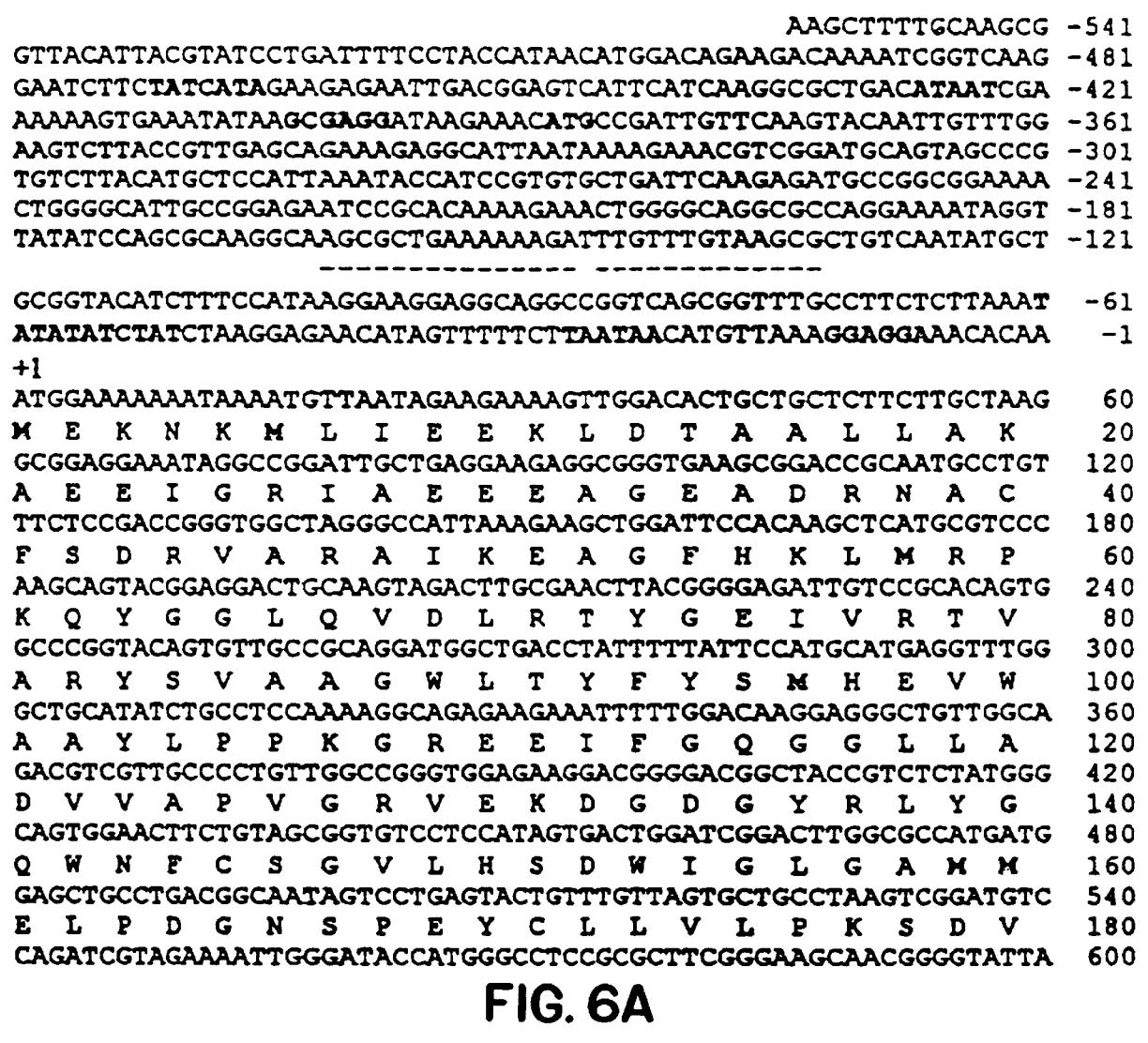

The PH is preferably produced by *E. coli* as a host microorganism using the DNA set forth in SEQ ID NO:1 (FIG. 6A and 6B). *E. coli* which is commonly used for this purpose as is well known to those skilled in the art. The phenol hydroxylase has the deduced amino acid sequence as set forth in SEQ ID NO: 1 (FIGS. 6A and 6B).

The DNA of SEQ ID NO:1 is incorporated into a plasmid (vector) and then transformed into the host microorganism. This can be done by electroporation, transfection and other well known methods of DNA transfer. The DNA used to produce the recombinant is contained in pGG01 of *Bacillus stearothermophilus* deposited as ATCC 67824. The phenol hydroxylase is contained in a 2.1 kb HindIII segment (pPH229; in ATCC 69891) or EcoR1 13.3 kb segment (pPH219) of pGG01. The host microorganism is *E. Coli* as previously discussed.

EXAMPLE 1

The catabolic gene pheA coding for the conversion of phenol to catechol was cloned from *Bacillus stearothermophilus* BR219 into *Escherichia coil*. Following its localization on the 11-kb *B. stearothermophilus* DNA insert by deletion and expression analysis, the phenol hydroxylase gene pheA was subcloned as a 2-kb HindIII fragment, whose transformant expressed the enzyme after phenol induction and even more strongly after o-, m-, and p-cresol induction. In vitro transcription-translation experiments indicated that the phenol hydroxylase and catechol 2,3-dioxygenase enzymes are constituted of single subunits with molecular weights of 44,000 and 33,000, respectively. Nucleotide sequencing of the pheA gene revealed a significant similarity to flavin hydroxylases from Rhodococcus and Streptomyces species. Hybridization experiments indicated that the fragment containing PheA and PheB is located on a 66-kb plasmid, pGG01, in the parental thermophile.

MATERIALS AND METHODS

Bacterial strains and culture conditions. *Bacillus stearothermophilus* BR219, an isolate obtained from contaminated river sediment, was maintained at 55° C. in DP minimal medium which is:

| | |
|---|---|
| $K_2HPO_4$ | 0.5 g/l |
| $NH_4Cl$ | 1.0 g/l |
| $MgSO_4.7H_2O$ | 20 mg/l |
| Yeast Extract | 0.2 g/l |
| Casamino Acids | 0.1 g/l |
| pH 7.2 | | containing 5 mM phenol as the major carbon source as previously described (Gurujeyalakshmi, G., et al., Appl. Environ. Microbiol. 55:500–502 (1989)). *Escherichia coli* XL-1 (recA (recAI lac endAI gyrA96 thi hsdR17 supE44 relA1 (F' proAB, lacIg, lacZIΔM15, Tn10))) (Bullock, W. O., et al., BioTechniques 4:376–379 (1987)), used for construction and maintenance of plasmids, was cultured at 37° C. on LB medium which is:
 10 g/l Bacto-tryptone
Tryptophan source, Difco, Detroit, Mich.
 5 g/l Bacto-yeast extract
Nitrogen source, Difco, Detroit, Mich.
 10 g/l NaCl
 pH 7.4
Plasmids were introduced into *E. coli* XL-1 by electroporation (Dower, W. J., et al., Nucleic Acids Res. 16:6127–6139 (1988)). Ampicillin at 50 μg/ml was used for selection of plasmids. Tetracycline at 12.5 μg/ml was also incorporated during growth of the *E. coli* XL-1 host as a precaution against contamination.

Genetic procedures. Plasmid DNA was isolated from *E. coli* by alkali lysis (Birnboim, H. C., et al., Nucleic Acids Res. 7:1513–1523 (1979)). *B. stearothermophilus* BR219 DNA was prepared by the method of Saito and Miura (Saito, H., et al., Biochim. Biophys. Acta 72:619–629 (1963)). DNA fragments were isolated from agarose gels by using USBioclean (United States Biochemical Corp. Cleveland, Ohio) and electroelution (IBI, New Haven, Conn.). Restriction enzymes, DNA ligase, and alkaline phosphatase were obtained from Boehringer Mannheim Co., Indianapolis, Ind. Southern hybridizations were performed as described by Maniatis et al (Maniatis, T., et al., Molecular cloning: a laboratory manual. Cold Spring Harbor Laboratory, Cold Spring Harbor, N.Y. (1982)) with American H-bond nylon membrane probed with DNA labelled with ($\alpha$-$^{32}$P)dCTP, using a Boeringer-Mannheim Co. random-primer labeling kit. Following hybridization, blots were washed at high stringency (43° C. in 0.1×SSC-0.1% sodium dodecyl sulfate (SDS)-50% formamide, where 1XSSC is 0.15 M NaCl with 0.015 M sodium citrate).

Screening for transformants carrying pheA and pheB. Transformants were spread on LB plates containing 1 mM phenol, 50 μg of ampicillin per ml, and 12.5 μg of tetracycline per ml and incubated overnight at 37° C. Colonies that became yellow (as a result of 2-hydroxymuconic semialdehyde) following spraying of a 0.1% of catechol solution were patched on LB plates containing 1 mM phenol. Colonies in which the yellow compound formed during growth without catechol addition were retained as putative carriers of both pheA and pheB.

Preparation of cell extracts and enzyme assays. Cells for enzyme analysis were grown in LB broth with 1 mM phenol and 50 μg of ampicillin per ml at 37° C. to mid-log phase, reinoculated into fresh medium of the same composition, and grown to late-exponential phase. The cells were harvested by centrifugation at 6,000×g for 10 min, washed twice in 50 mM sodium phosphate buffer (pH 7.5), disrupted sonically by six 30-s bursts with an ultrasonic homogenizer (Cole-Palmer Instrument Co., Chicago, Ill.), and centrifuged at 12,000×g for 30 minutes. The clear supernatant was used as a crude enzyme extract. Phenol hydroxylase was assayed in the supernatant as described by Gurujeyalakshmi and Oriel (Appl. Environ. Microbiol. 55:500–502 (1989)). Catechol 2,3-dioxygenase was assayed as described by Nozaki (Nozaki, M., Methods Enzymol. 17A:522–525 (1970)). Protein was measured by the method of Lowry et al (Lowry, O. H., et al., J. Biol. Chem. 193:265–275 (1951)) with bovine serum albumin for standardization. One unit of enzyme activity is defined as the amount causing the disappearance of 1 μmol of phenol per min at 55° C. for phenol hydroxylase or the appearance of 1 μmol of 2-hydroxymuconic semialdehyde per min at ambient temperature for catechol 2,3-dioxygenase.

Nucleotide sequence determinations. Plasmid vector pBluescript SK- (Stratagene, LaJolla, Calif.) was used to construct the subclones for DNA sequencing. Serial deletion of subclones was made by using the exo/mung system (Stratagene). Nucleotide sequences were determined directly from plasmids by the dideoxy-chain termination method (Sanger, F., et al., Proc. Natl. Acad. Sci. USA 74:5463–5467 (1977)) with T7 DNA polymerase (Sequenase; United States Biochemical Corp.). The dITP was substituted for dGTP to eliminate band compression in GC-rich regions. Wedge gels 0.2 to 0.6 mm thick were used in electrophoresis to increase resolution. Other sequencing procedures were performed by published methods (Maniatis, T., et al., Molecular cloning: a laboratory manual. Cold Spring Harbor Laboratory, Cold Spring Harbor, N.Y. (1982)). Nucleotide and deduced amino acid sequences were analyzed by the GCG DNA analysis program (Genetics Computer Group, Inc., Madison, Wis.).

In vitro transcription-translation and activity staining of the SDS-polyacrylamide gel. The protein products of cloned B. stearothermophilus DNA inserts were identified with a DNA-directed transcription-translation system involving E. coli cell extracts (Amersham Life Sciences, Arlington Heights, Ill.). Proteins produced from plasmids (1 μg per reaction) were radioactively labeled with L-($^{35}$S) methionine in 50-min incubation periods and a 30-min (cold) methionine chase reaction. Samples were separated on SDS-10% polyacrylamide gels and protein bands were observed by radioautography. The catechol 2,3-dioxygenase band was located by formation of yellow 2-hydroxymuconic semialdehyde formed after gel immersion in 0.1% catechol. Prestained protein molecular size markers (GIBCO BRL, Life Technologies, Inc. Gaithersburg, MD) were used.

Nucleotide sequence accession number. The GenBank accession number of pheA is U17960.

RESULTS

Cloning and expression of pheA. Mixed plasmid and chromosomal DNA was extracted from B. stearothermophilus BR219 and partially cleaved with EcoRI, and fragments ranging from 9 to 20 kb were obtained by gel electrophoresis and electroelution for ligation with pBluescriptI SK-. Transformants of E. coli XL-1 were grown on LB plates containing ampicillin and phenol and those demonstrating 2-hydroxymuconic semialdehyde formation after being sprayed with 0.1% catechol were retained as putative transformants carrying the pheB gene. Subsequent examination of these transformants yielded EC390, a recombinant which did not grow on phenol but demonstrated production of 2-hydroxymuconic semialdehyde on LB plates containing 1 mM phenol, suggesting the presence of both pheA and pheB encoding the first two steps of the phenol pathway. The plasmid isolated from this recombinant, designated pPH219, contained a 13.3 kb EcoRI insert. To locate pheA and pheB within this insert, measurements of phenol hydroxylase and catechol 2,3-dioxygenase in transformants with insert deletions were carried out by using determined restriction sites. As shown in FIG. 1, both pheA and pheB were located in the 6-kb EcoRI- ClaI DNA fragment cloned in plasmid pPH219-5, and pheA was found in the 2.1 kb HindIII DNA fragment cloned in plasmid pPH229.

Figure 2:
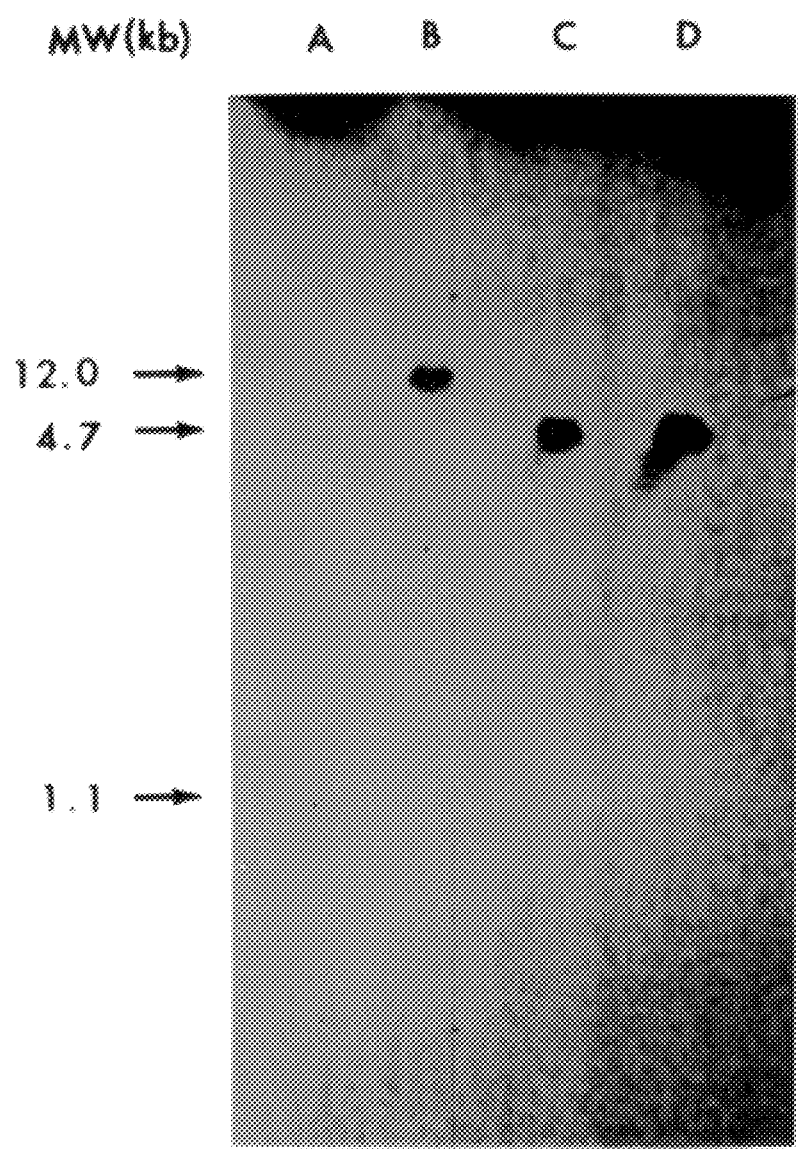
FIG. 2 is a Southern blot analysis of genomic DNA and the cryptic plasmid pGG01 which hybridized with the cloned DNA containing pheA and pheB which was labeled with [$\alpha$-$^{32}$P]dCTP. Lanes A, EcoRI-digested BR219 genomic DNA; B and C, BamHI- and EcoRI-digested cryptic plasmid pGG01;D, EcoRI-digested pPH219.

Localization of pheA and pheB in B. stearothermophilus BR219. B. stearothermophilus BR219 carries a 66-kb low-copy-number plasmid designated pGG01. With the 10.3-kb EcoRI insert of plasmid pPH219 as a probe, Southern hybridization analysis was carried out with EcoRI and BamHI-digested BR219 genomic and plasmid DNA. The cloned insert carrying pheA and pheB hybridized with plasmid but not chromosomal DNA (FIG. 2), indicating that plasmid pGG01 encodes at least part of the phenol catabolic pathway.

Figure 3:
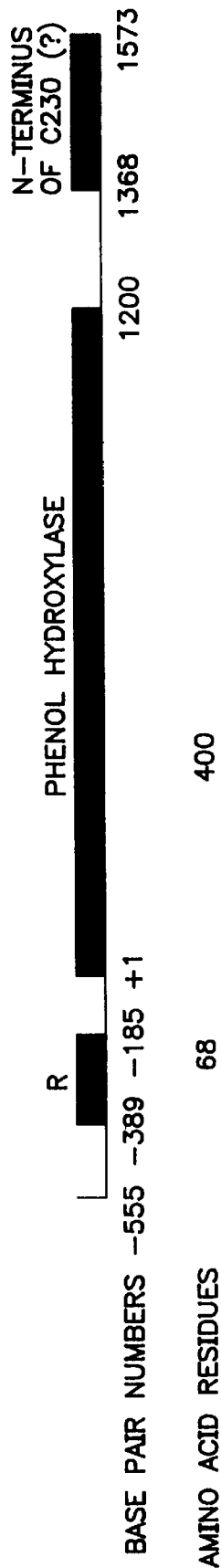
FIG. 3 is a map showing a structural analysis of the 2.1-kb HindIII fragment. R designates an ORF of unknown function. C230 is catechol 2,3-dioxygenase.

Structural analysis of the phenol hydroxylase gene and gene product. To determine the structure of the phenol hydroxylase gene, nucleotide sequencing of the 2.1-kb HindIII fragment (pPH229) was carried out. As shown in FIGS. 6A and 6B (SEQ ID NO:1), one open reading frame (ORF) was found encompassing 1,200 nucleotides encoding a protein of 400 amino acids. The insert also contains about 556 and 373 bp of 5'- and 3'-flanking sequences, respectively. Putative promoter regions, TATATATCTAT and TAATAA, are present from −61 to −51 and from −29 to −24, respectively, from the translational initiation site. A putative Shine-Dalgarno sequence, GGAGAA, was present at the −13 position. The sequence revealed two small additional open reading frames (FIG. 3). The first ORF is upstream of pheA, starting at −389 and ending at −185, with putative promoter regions from −472 to −466 (TATCATA) and from −428 to −423 (ATAAT) and Shine-Dalgarno sequence (−414 to −409 (GCGAGG)). The function of this short ORF, which is designated R, is not known. Another ORF starts downstream of pheA at 1368 without termination. Since the deletion experiments indicated that pheB was in proximity downstream of pheA, it is possible that this is the N terminus of the catechol 2,3-dioxygenase gene.

TABLE 1

Induction of phenol hydroxylase and catechol 2,3-dioxygenase in *E. coli*

| Plasmid | Act of phenol hydroxylase (U/mg of protein) | | Act of catechol 2,3-dioxygenase (U/mg of protein) | |
|---|---|---|---|---|
| | −phenol | +phenol | −phenol | +phenol |
| SK-1 | 0 | 0 | 0 | 0 |
| pPH219-5 | 0.42 | 0.54 | 0.57 | 0.74 |
| pPH222 | 0.88 | 1.07 | 0.59 | 0.84 |
| pPH223 | 1.11 | 0.83 | 0.67 | 0.97 |
| pPH224 | 0.87 | 0.9 | 0 | 0 |
| pPH229 | 0.12 | 0.72 | 0 | 0 |

Figure 4:
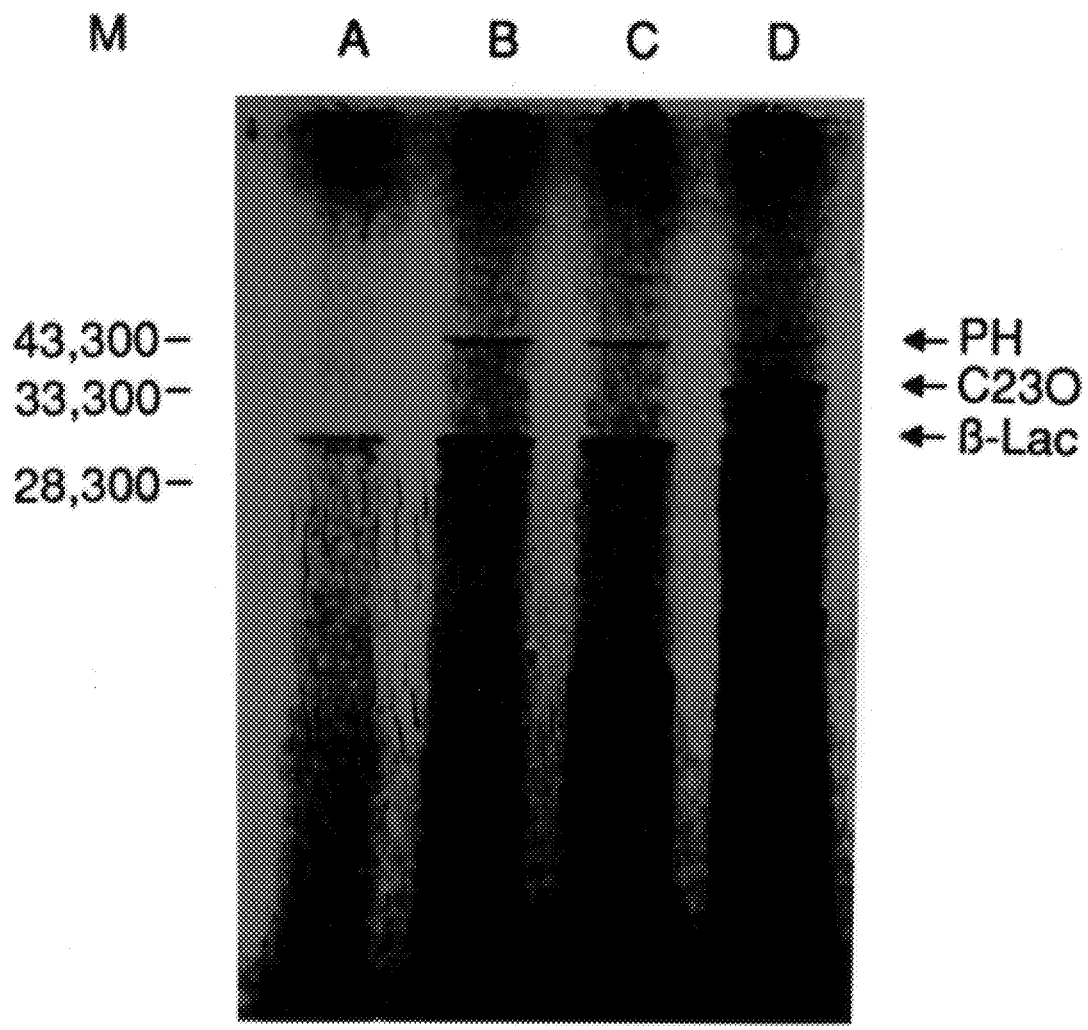
FIG. 4 is an electrophoresis gel showing proteins synthesized by in vitro transcription-translation. Lanes: M, molecular weight markers; A, pbluescript SK- vector; B, pPH229; C, pPH224; D, pPH223. The upper, middle, and lower arrows point to the phenol hydroxylase (PH), catechol 2,3-dioxygenase (C230), and β-lactamase (β-Lac), respectively.

Molecular mass of phenol hydroxylase and catechol 2,3-dioxygenase. Transcription-translation results (FIG. 4) indicated a protein of 43,000 Da expressed from pPH229, which encodes the pheA gene. This value is in excellent agreement with the 43,000 Da deduced from pheA sequencing data. For pPH223, which encodes both pheA and pheB, an additional 33,000-Da band is seen. Activity staining by gel immersion in 0.1% catechol, yielding yellow 2-hydroxymuconic semialdehyde, was used for identification of this protein as the pheB transcription-translation product (data not shown). The lower-molecular-mass band in FIG. 4, lane C, may also be the product of pheB, which is truncated in pPH224. Other lower-moelcular-mass bands expressed in lanes C and D by subclones containing DNA regions upstream and downstream, respectively, of the sequenced insert of pPH229 have not been identified.

Figure 5:
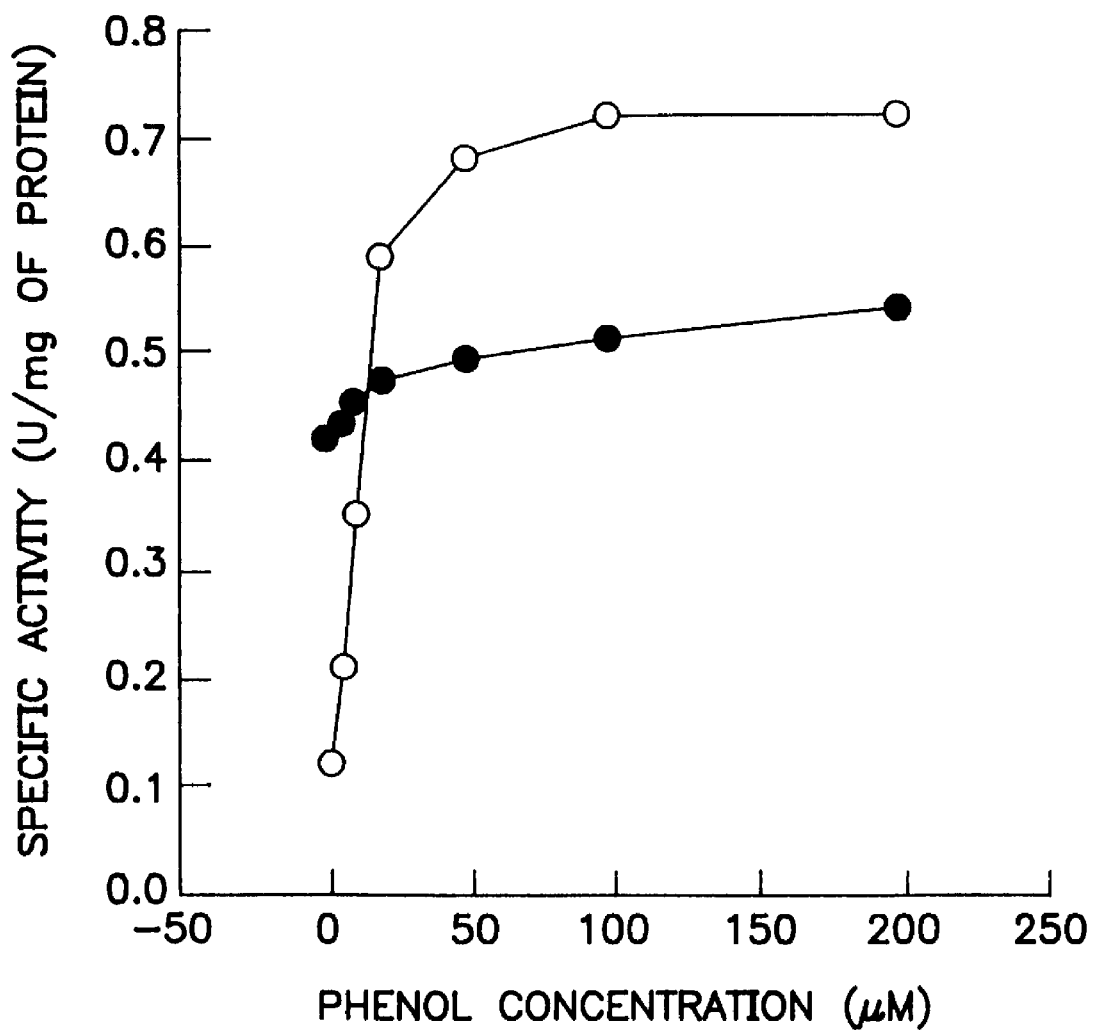
FIG. 5 is a graph showing the effect of phenol concentration on phenol hydroxylase induction. O, phenol hydroxylase produced by *E. coli* containing pPH229; ●, phenol hydroxylase produced by *E. coli* containing pPH219-5.

Expression and inducibility of phenol hydroxylase and catechol 2,3-dioxygenase genes in *E. coli*. The phenol path in the BR219 thermophile parent is induced by phenol (Gurujeyalakshmi, G., et al., Appl. Environ. Microbiol. 55:500–502 (1989)). To determine whether the cloned insert in pPH219 contained phenol regulatory elements from parental BR219, transformants containing this plasmid and those of the deletions shown in FIG. 1 were tested for differences in phenol hydroxylase expression in cells grown at different phenol concentrations. As shown in Table 1, in *E. coli* bearing plasmid pPH219 or most of the deletions, phenol hydroxylase and catechol 2,3-dioxygenase specific activities were either unaltered or only slightly increased by growth in the presence of phenol. In pPH229, however, phenol hydroxylase expression demonstrated marked dependence on phenol. A comparison of differences in phenol hydroxylase induction for pPH229 and pPH219-5 with phenol concentration is presented in FIG. 5, which shows that pPH229 demonstrates marked phenol dependence at concentrations up to 20 μM. The level of induction of phenol hydroxylase in this pPH229 by other aromatics is shown in Table 2, which shows that enzyme levels induced by o-, m-, and p-cresol were even higher than that induced by phenol.

TABLE 2

Induction of phenol hydroxylase by aromatic compounds

| Inducer | sp act of phenol hydroxylase (U/mg of protein) |
|---|---|
| None | 0.12 |
| Phenol | 0.54 |
| Benzoate | 0.11 |
| Toluate | 0.11 |
| o-Cresol | 1.48 |
| m-Cresol | 1.6 |
| p-Cresol | 1.46 |
| 2-Chlorophenol | 0.42 |

Expression of phenol hydroxylase in the recombinant bearing pPH229 is induced by phenol and even more strongly by cresols. Since the BR219 phenol hydroxylase is also active on cresols, degradation of cresols in the environment may be an important function of the pathway. The lack of phenol hydroxylase induction in transformants pPH219-5, pPH222, pPH223, and pPH224, which contain the catechol 2,3-dioxygenase gene and/or DNA segments upstream of the pheA gene, is not yet understood but suggests a complex regulatory mechanism which may involve the small ORF designated R adjacent to pheA.

The recombinant *Escherichia coli* containing a gene encoding the phenol hydroxylase had the ability to produce indigo and indirubin. This result was unexpected since there was no evidence of this result in *Bacillus Stearothermophilus*. The results can be seen from the following examples.

EXAMPLE 2

This Example shows the production of indigo and indirubin.

*Escherichia coli* XL-1 constructs containing plasmids pPH219, pPH222, pPH223, or pPH224 were grown in LB broth (Example 1) containing 1 mM phenol and 50 micrograms per ml ampicillin for 24 hours as 50 ml cultures in a 125 ml flask with shaking at 37° C. The cultures containing bacterial cells and insoluble pigment were centrifuged at 10,000 rpm in a Sorvall SS34 Rotor (Dupont/Sorvall, Wilmington, Del.) for 10 minutes, and following removal of supernatant, the precipitate was extracted with 10 ml chloroform and centrifuged again. When measured using visible absorption spectroscopy, the purple supernatant showed absorption bands at both 560 and 610 nm. Upon paper chromatography, blue and pink bands were resolved which were identified as indigo and indirubin, respectively following extraction from the chromatogram and examination with combined gas chromatography and mass spectrometry.

EXAMPLE 3

This Example show kinetics of indigo and indirubin formation

The amount of indigo and indirubin produced in culture is dependent on the culture age, with indigo produced preferentially at earlier times when more dissolved oxygen is available. *E. Coli* XL-1 containing pPH219 was grown in 50 ml LB culture containing 50 mg/ml ampicillin and 1 mMphenol. Production of indigo and indirubin was observed by visible spectral analysis following solubilization of the formed pigments in chloroform as described in Example 2.

TABLE 3

Production of indigo and indirubin with time in culture

| Culture Time (h) | OD(610) | OD(560) | Ratio |
|---|---|---|---|
| 18 | 0.025 | 0.016 | 1.56 |
| 24 | 0.695 | 0.590 | 1.78 |
| 30 | 0.660 | 0.706 | 0.934 |
| 42 | 0.536 | 0.727 | 0.74 |

As can be seen in Table 3, indigo with maximum absorption at 610 nm is produced in highest quantity at 24h, whereas indirubin with maximum absorption at 560 nm is produced in highest quantity after 40 hours.

EXAMPLE 4

Influence of dissolved oxygen on formation of indigo and indirubin.

The indigo/indirubin ratio produced varied with the oxygen available to the culture and could be regulated in this manner. This was observed by coloration of colonies of the constructs in Example 2 growth on LB agar plates which also contained 1 mM phenol and 50 μg/ml ampicillin. The center of the colonies were pink, whereas the outer edges were blue where oxygen was present. This effect could also be observed in liquid culture by altering culture oxygenation by using different volumes of culture medium for growth in identical flasks. For this purpose, E. coli XL-1 containing plasmid pPH219 was grown in 125 ml flasks containing varied amounts of LB medium supplemented with ampicillin at 50 μg/ml and phenol at 1 mM were grown at 37° C. for 24 hours followed by extraction of the pigments into chloroform as described in Example 2. As shown in Table 4 for pPH219, the ratio of absorption at 610 nm (the absorption maximum for indigo) to that at 560 nm (the absorption maximum for indirubin) varied with the culture volume, with the most highly aerated cultures with small volume producing the highest amounts of indigo.

TABLE 4

Variation in indigo and indirubin formation with culture aeration.

| Culture Volume (ml) | RATIO OD (610 nm)/ OD(560 nm) |
|---|---|
| 10 | 0.88 |
| 20 | 0.88 |
| 30 | 0.66 |
| 40 | 0.33 |
| 50 | 0.29 |
| 60 | 0.28 |
| 70 | 0.27 |
| 80 | 0.30 |
| 100 | 0.28 |

The phenol hydroxylase of the present invention derived from *Bacillus stearothermophilus* is monooxygenase and is stable at elevated temperatures. The prior art naphthlene dioxgenase from *Pseudomonas putida* tends to be unstable as reported in the literature and is composed of multiple units.

It is believed that tryptophan is converted to indole by tryptophanase in the *E. coli* by an oxidation mechanism. The coupling takes place without any other added precursors. Thus the *E. coli* must be able to produce tryptophan either naturally or by transformation.

As seen from Table 1, the presence of the phenol hydroxylase gene allows the production of indigo and indirubin even without the phenolic compound. The use of the phenolic compound is preferred.

The foregoing description is only illustrative of the present invention and the present invention is limited only by the hereinafter appended claims.

We claim:

1. An isolated and purified DNA encoding a *Bacillus stearothermophilus* phenol hydroxylase, having a DNA sequence as set forth in SEQ ID NO:1.

2. An isolated and purified DNA which encodes a phenol hydroxylase comprising the DNA contained in pPH229 in *Escherichia coli* deposited as ATCC 69891.

3. A recombinant plasmid containing a segment of DNA encoding a *Bacillus stearothermophilus* phenol hydroxylase, having a sequence as set forth in SEQ ID NO:1.

4. A recombinant plasmid which encodes a phenol hydroxylase comprising the DNA contained in pPH229 in *Escherichia coli* deposited as ATCC 69891.

5. A recombinant plasmid containing a segment of DNA encoding phenol hydroxylase, wherein the DNA is a 2.1 kb segment of the DNA in plasmid pGG01 of *Bacillus stearothermophilus* deposited as ATCC 67824.

6. The plasmid of claim 5 wherein the segment of DNA is in a HindIII subsegment of the segment.

7. The plasmid of claim 5 wherein the segment is 13.3 kb in length and restricted by EcoRI.

8. An *Escherichia coli* cell containing a recombinant plasmid with a segment of DNA of *Bacillus stearothermophilus* encoding a phenol hydroxylase having a sequence as set forth in SEQ ID NO:1.

9. An *Escherichia coli* cell containing a recombinant plasmid containing a segment of DNA encoding a phenol hydroxylase, wherein the segment of DNA is a 13.3 kb EcoRI- restricted DNA segment contained in plasmid pGG01 of *Bacillus stearothermophilus* deposited as ATCC 67824.

10. An *Escherichia coli* cell containing a recombinant plasmid containing a segment of DNA encoding a phenol hydroxylase, wherein the segment of DNA is a 2.1 kb subsegment of the DNA in plasmid pGG01 of *Bacillus stearothermophilus* deposited as ATCC 67824.

11. The *Escherichia coli* cell of claim 10 wherein the DNA is in a HindIII subsegment of the segment.

12. The *Escherichia coli* cell of claim 10 wherein the segment of DNA is contained in pPH229 in *Escherichia coli* deposited as ATCC 69891.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1573
        ( B ) TYPE: Nucleic Acid
        ( C ) STRANDEDNESS: Single
        ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
        ( A ) ORGANISM: Bacillus stearothermophilus
        ( B ) STRAIN: ATCC 67824
        ( C ) INDIVIDUAL ISOLATE: N/A
        ( D ) DEVELOPMENTAL STAGE: N/A
        ( E ) HAPLOTYPE: N/A
        ( F ) TISSUE TYPE: N/A ( G ) CELL TYPE: N/A
( H ) CELL LINE: N/A
( I ) ORGANELLE: N/A ( v i i ) IMMEDIATE SOURCE: N/A ( v i i i ) POSITION IN GENOME: N/A ( i x ) FEATURE:
( A ) NAME/KEY: encodes phenol hydroxylase
pheA
( B ) LOCATION:
( C ) IDENTIFICATION METHOD: sequencing
( D ) OTHER INFORMATION:

( x ) PUBLICATION INFORMATION:
( A ) AUTHORS: Kim, Cheol, Oriel, Patrick J.
( B ) TITLE: Characterization of the
Bacillus stearothermophilus
BR219 Phenol Hydroxylase Gene
( C ) JOURNAL: American Society for Microbiology
( D ) VOLUME: 61
( E ) ISSUE: 4
( F ) PAGES: 1252-1256
( G ) DATE: 1995
( K ) RELEVANT RESIDUES IN SEQ ID NO: In SEQ ID NO: 1 From 1
to 1260.

( x i ) SEQUENCE DESCRIPTION: SEQ ID NO:1:

| ATG | GAA | AAA | AAT | AAA | ATG | TTA | ATA | GAA | GAA | AAG | TTG | GAC | ACT | GCT | 45 |
| Met | Glu | Lys | Asn | Lys | Met | Leu | Ile | Glu | Glu | Lys | Leu | Asp | Thr | Ala | |
| | | | | 5 | | | | | 10 | | | | | 15 | |

| GCT | CTT | CTT | GCT | AAG | GCG | GAG | GAA | ATA | GGC | CGG | ATT | GCT | GAG | GAA | 90 |
| Ala | Leu | Leu | Ala | Lys | Ala | Glu | Glu | Ile | Gly | Arg | Ile | Ala | Glu | Glu | |
| | | | | 20 | | | | | 25 | | | | | 30 | |

| GAG | GCG | GGT | GAA | GCG | GAC | CGC | AAT | GCC | TGT | TTC | TCC | GAC | CGG | GTG | 135 |
| Glu | Ala | Gly | Glu | Ala | Asp | Arg | Asn | Ala | Cys | Phe | Ser | Asp | Arg | Val | |
| | | | | 35 | | | | | 40 | | | | | 45 | |

| GCT | AGG | GCC | ATT | AAA | GAA | GCT | GGA | TTC | CAC | AAG | CTC | ATG | CGT | CCC | 180 |
| Ala | Arg | Ala | Ile | Lys | Glu | Ala | Gly | Phe | His | Lys | Leu | Met | Arg | Pro | |
| | | | | 50 | | | | | 55 | | | | | 60 | |

| AAG | CAG | TAC | GGA | GGA | CTG | CAA | GTA | GAC | TTG | CGA | ACT | TAC | GGG | GAG | 225 |
| Lys | Gln | Tyr | Gly | Gly | Leu | Gln | Val | Asp | Leu | Arg | Thr | Tyr | Gly | Glu | |
| | | | | 65 | | | | | 70 | | | | | 75 | |

| ATT | GTC | CGC | ACA | GTG | GCC | CGG | TAC | AGT | GTT | GCC | GCA | GGA | TGG | CTG | 270 |
| Ile | Val | Arg | Thr | Val | Ala | Arg | Tyr | Ser | Val | Ala | Ala | Gly | Trp | Leu | |
| | | | | 80 | | | | | 85 | | | | | 90 | |

| ACC | TAT | TTT | TAT | TCC | ATG | CAT | GAG | GTT | TGG | GCT | GCA | TAT | CTG | CCT | 315 |
| Thr | Tyr | Phe | Tyr | Ser | Met | His | Glu | Val | Trp | Ala | Ala | Tyr | Leu | Pro | |
| | | | | 95 | | | | | 100 | | | | | 105 | |

| CCA | AAA | GGC | AGA | GAA | GAA | ATT | TTT | GGA | CAA | GGA | GGG | CTG | TTG | GCA | 360 |
| Pro | Lys | Gly | Arg | Glu | Glu | Ile | Phe | Gly | Gln | Gly | Gly | Leu | Leu | Ala | |
| | | | | 110 | | | | | 115 | | | | | 120 | |

| GAC | GTC | GTT | GCC | CCT | GTT | GGC | CGG | GTG | GAG | AAG | GAC | GGG | GAC | GGC | 405 |
| Asp | Val | Val | Ala | Pro | Val | Gly | Arg | Val | Glu | Lys | Asp | Gly | Asp | Gly | |
| | | | | 125 | | | | | 130 | | | | | 135 | |

| TAC | CGT | CTC | TAT | GGG | CAG | TGG | AAC | TTC | TGT | AGC | GGT | GTC | CTC | CAT | 450 |
| Tyr | Arg | Leu | Tyr | Gly | Gln | Trp | Asn | Phe | Cys | Ser | Gly | Val | Leu | His | |
| | | | | 140 | | | | | 145 | | | | | 150 | |

| AGT | GAC | TGG | ATC | GGA | CTT | GGC | GCC | ATG | ATG | GAG | CTG | CCT | GAC | GGC | 495 |
| Ser | Asp | Trp | Ile | Gly | Leu | Gly | Ala | Met | Met | Glu | Leu | Pro | Asp | Gly | |
| | | | | 155 | | | | | 160 | | | | | 165 | |

| AAT | AGT | CCT | GAG | TAC | TGT | TTG | TTA | GTG | CTG | CCT | AAG | TCG | GAT | GTC | 540 |
| Asn | Ser | Pro | Glu | Tyr | Cys | Leu | Leu | Val | Leu | Pro | Lys | Ser | Asp | Val | |
| | | | | 170 | | | | | 175 | | | | | 180 | |

| CAG | ATC | GTA | GAA | AAT | TGG | GAT | ACC | ATG | GGC | CTC | CGC | GCT | TCG | GGA | 585 |
| Gln | Ile | Val | Glu | Asn | Trp | Asp | Thr | Met | Gly | Leu | Arg | Ala | Ser | Gly | |

```
                           1 8 5                           1 9 0                           1 9 5
AGC   AAC   GGG   GTA   TTA   GTT   GAA   GGT   GCT   TAT   GTT   CCA   TTA   CAC   CGG        630
Ser   Asn   Gly   Val   Leu   Val   Glu   Gly   Ala   Tyr   Val   Pro   Leu   His   Arg
                        200                           205                           210

ATC   TTT   CCG   GCT   GGC   CGG   GTG   ATG   GCT   CAT   GGG   AAG   CCA   GTG   GGA        675
Ile   Phe   Pro   Ala   Gly   Arg   Val   Met   Ala   His   Gly   Lys   Pro   Val   Gly
                        215                           220                           225

GGC   GAT   TAC   GAC   GAG   AAT   GAT   CCG   GTA   TAT   CGC   ATG   CCA   TTT   ATG        720
Gly   Asp   Tyr   Asp   Glu   Asn   Asp   Pro   Val   Tyr   Arg   Met   Pro   Phe   Met
                        230                           235                           240

CCG   CTT   TTC   TTG   CTT   GGG   TTC   CCT   TTA   GTA   TCT   TTA   GGC   GGC   GAC        765
Pro   Leu   Phe   Leu   Leu   Gly   Phe   Pro   Leu   Val   Ser   Leu   Gly   Gly   Asp
                        245                           250                           255

GAA   CGA   TTG   GTG   TCA   CTT   TTC   CAA   GAA   CGC   ACT   GAG   AAG   CGC   ATT        810
Glu   Arg   Leu   Val   Ser   Leu   Phe   Gln   Glu   Arg   Thr   Glu   Lys   Arg   Ile
                        260                           265                           270

CGT   GTC   TTC   AAA   GGC   GGC   GCG   AAA   GAA   AAG   GAT   TCT   GCC   GCT   AGC        855
Arg   Val   Phe   Lys   Gly   Gly   Ala   Lys   Glu   Lys   Asp   Ser   Ala   Ala   Ser
                        275                           280                           285

CAG   CGG   CTG   TTA   GCC   GAG   ATG   AAA   ACA   GAA   TTA   AAT   GCA   ATG   GAA        900
Gln   Arg   Leu   Leu   Ala   Glu   Met   Lys   Thr   Glu   Leu   Asn   Ala   Met   Glu
                        290                           295                           300

GGC   ATT   GTG   GAA   CAA   TAT   ATC   CGC   CAG   CTT   GAG   GCT   TGC   CAA   AAA        945
Gly   Ile   Val   Glu   Gln   Tyr   Ile   Arg   Gln   Leu   Glu   Ala   Cys   Gln   Lys
                        305                           310                           315

GAA   GGA   AAG   ACG   GTG   ATG   AAC   GAT   ATG   GAG   CGA   GAG   CAG   CTA   TTC        990
Glu   Gly   Lys   Thr   Val   Met   Asn   Asp   Met   Glu   Arg   Glu   Gln   Leu   Phe
                        320                           325                           330

GCA   TGG   CGT   GGA   TAT   GTG   GCA   AAA   GCG   TCC   GCC   AAT   ATT   GCC   GTC       1035
Ala   Trp   Arg   Gly   Tyr   Val   Ala   Lys   Ala   Ser   Ala   Asn   Ile   Ala   Val
                        335                           340                           345

AGA   ACA   CTG   TTA   ACT   CTT   GGA   GGC   AAT   TCG   ATC   TTT   AAA   GGC   GAT       1080
Arg   Thr   Leu   Leu   Thr   Leu   Gly   Gly   Asn   Ser   Ile   Phe   Lys   Gly   Asp
                        350                           355                           360

CCG   GTA   GAA   CTG   TTC   ACA   AGA   GAT   TTG   CTA   GCG   GTG   GCC   GCA   CAT       1125
Pro   Val   Glu   Leu   Phe   Thr   Arg   Asp   Leu   Leu   Ala   Val   Ala   Ala   His
                        365                           370                           375

CCT   AAC   TCC   CTG   TGG   GAG   GAT   GCG   ATG   GCT   GCA   TAT   GGA   AGA   ACG       1170
Pro   Asn   Ser   Leu   Trp   Glu   Asp   Ala   Met   Ala   Ala   Tyr   Gly   Arg   Thr
                        380                           385                           390

ATA   TTC   GGG   CTG   CCA   GGG   GAC   CCA   GTC   TGG   TAAGACAGCA   GCAGAATGTG          1220
Ile   Phe   Gly   Leu   Pro   Gly   Asp   Pro   Val   Trp
                        395                           400

TGTTTATAAA   GATTTTCAAA   AAATTCATTT   CTTTGGTGAA   AGAAAATGGA   TTTCACACAA    1280

AATTTAAACC   AATGAACCCA   ATTGGATCGT   TCGCGTCCAT   TTCACCAATA   TACAAAAAAA    1340

CAGCAGAAAA   GGAGACGGAT   ACCGGTGGAT   GACCGTTTGT   TTCGCAACGT   AATGGGGACA    1400

TTTGCCACAG   GGGTGACAGT   CATAACGACA   GAGATCGACG   GGGATATACA   CGGCATGACT    1460

GCAAATGCGT   TTATGTCCGT   ATCGTTACAT   CCAAAATTGG   TGCTTATTTC   GATTGGCGAA    1520

AAAGCAAAGA   TGCGGGAGCG   TATCAAAAAA   TCGAAAACGT   ATGCAGTAAG   CTT           1573
```